(12) United States Patent
Kajii

(10) Patent No.: US 7,295,319 B2
(45) Date of Patent: Nov. 13, 2007

(54) METHOD FOR MEASURING CONCENTRATION OF NITROGEN DIOXIDE IN AIR BY SINGLE-WAVELENGTH LASER INDUCED FLUORESCENCE METHOD, AND APPARATUS FOR MEASURING CONCENTRATION OF NITROGEN DIOXIDE BY THE METHOD

(75) Inventor: Yoshizumi Kajii, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 468 days.

(21) Appl. No.: 10/494,268

(22) PCT Filed: May 31, 2002

(86) PCT No.: PCT/JP02/05363

§ 371 (c)(1),
(2), (4) Date: May 4, 2004

(87) PCT Pub. No.: WO03/040707

PCT Pub. Date: May 15, 2003

(65) Prior Publication Data

US 2004/0262501 A1    Dec. 30, 2004

(30) Foreign Application Priority Data

Nov. 5, 2001  (JP) .............................. 2001-339857

(51) Int. Cl.
*G01N 21/00* (2006.01)
(52) U.S. Cl. ...................... 356/433; 356/437
(58) Field of Classification Search ............... 356/317, 356/318, 432, 433, 435, 437–440
See application file for complete search history.

(56) References Cited

U.S. PATENT DOCUMENTS 3,970,430 A  *  7/1976  Reader et al. ............... 436/116

(Continued)

FOREIGN PATENT DOCUMENTS

JP         3-140843         6/1991

(Continued)

OTHER PUBLICATIONS

S.E. Schwartz et al, Kinetics of Nitrogen Dioxide Fluorescence, Aug. 1969, The Journal of Chemical Physics, vol. 1, No. 4, pp. 1286-1302.*

(Continued)

*Primary Examiner*—Layla G. Lauchman
(74) *Attorney, Agent, or Firm*—Westerman, Hattori, Daniels & Adrian, LLP.

(57) ABSTRACT

A method and apparatus for measuring the concentration of a trace nitrogen dioxide contained in the atmosphere on a pptv level with excellent accuracy by a single-wavelength laser induced fluorescence method. The device comprises a laser light source unit, a light excitation unit, a light guide unit, an air passing unit for passing either the air to be measured or a reference air prepared by removing nitrogen dioxide from the air to be measured, a light sensor unit and a control unit. A single-wavelength laser beam is applied to the air to be measured and the reference air. The intensity of the light emitted from the air to be measured and the intensity of the light emitted from the reference air are measured, and the concentration of nitrogen dioxide is determined by using the difference between the two.

19 Claims, 5 Drawing Sheets

U.S. PATENT DOCUMENTS 6,791,689 B1 * 9/2004 Weckstrom .................. 356/437

FOREIGN PATENT DOCUMENTS

| | | |
|---|---|---|
| JP | 7-63683 | 3/1995 |
| JP | 7-151686 | 6/1995 |
| JP | 8-159971 | 6/1996 |
| JP | 8-233706 | 9/1996 |

OTHER PUBLICATIONS

Komazaki et al, A new measurement method for nitrogen oxides in the air using an annular diffusion scrubber coated with titanium dioxide, Nov. 1999, Atmospheric Environment, vol. 33, Issue 27, pp. 4363-4371.*

Matsumi et al, High-Sensitivity Instrument for Measuring Atmospheric NO2, Nov. 2001, Analytical Chemistry, vol. 73, No. 22, pp. 5485-5493.*

J. Matsumoto et al.; Atmospheric Environment, vol. 35, No. 16, pp. 2803-2814, Jun. 2001. Cited in the PCT search report.

A. Matsumoto, 42th Japan Society of Atmospheric Environment Nenkai Koen Yoshishu, p. 299, Sep. 20, 2001. Cited in the PCT search report.

Notification of Transmittal of Copies of Translation of the International Preliminary Examination Report dated Jul. 22, 2004 and received by our foreign associate on Jul. 26, 2004.

* cited by examiner

METHOD FOR MEASURING CONCENTRATION OF NITROGEN DIOXIDE IN AIR BY SINGLE-WAVELENGTH LASER INDUCED FLUORESCENCE METHOD, AND APPARATUS FOR MEASURING CONCENTRATION OF NITROGEN DIOXIDE BY THE METHOD

TECHNICAL FIELD

The present invention relates to a method and an apparatus for determining a concentration of nitrogen oxide that is contained as a trace constituent in the atmosphere.

BACKGROUND ART

Ozone in the troposphere is thought to determine the oxidizing power of an atmosphere and further to bring about the global warming and to exert adverse influences on living bodies. In recent years a rising tendency of the tropospheric ozone has been suggested, and it is of urgent necessity to make clear the mechanism of ozone formation and extinction on the global scale. In order to elucidate the mechanism of ozone formation and extinction, it is essential to verify the photochemical theory in a clean area which has not been affected by unnatural pollution.

Nitrogen oxides $NO_x$ (nitrogen monoxide NO and nitrogen dioxide $NO_2$), which through photochemical reactions act as precursors of ozone and also are precursors of nitric acid, the substance forming acid rain, are thus extremely important species in the tropospheric photochemistry.

The concentration of nitrogen oxides in a clear atmosphere is thought to be several to several tens of pptv (the volume concentration unit in $10^{-12}$). Estimating the amount of formation of ozone in a clean area saved from air pollution requires a supersensitive nitrogen oxide concentration meter. Further, nitrogen dioxide and nitrogen monoxide are quickly transformed to each other by photochemical reactions in the daytime, and their time constants of transformation in the neighborhood of ground surface are generally around several minutes. It is thus necessary to hold down the measuring time to around 1 minute or less and it is required to complete the measurement in an extremely short period of time.

In the high-sensitivity measurement of the concentration of nitrogen oxides, use has so far been made of the chemiluminescence technique that detects a chmiluminescent light emitted when ozone reacts with nitrogen monoxide. If this technique is applied to measuring the concentration of nitrogen dioxide, nitrogen dioxide must for measurement of its concentration be first transformed to nitrogen monoxide through photodissociation or catalytic reaction. Further, this technique when used to complete the measurement in a measuring time of 1 minute has a limit of detection of 10 pptv, which is insufficient to measure the concentration of nitrogen dioxide in the clean atmosphere. Furthermore, the chemiluminescence technique, being an indirect method of measurement in which the concentration of nitrogen dioxide cannot be measured unless it is first transformed into nitrogen monoxide, has the shortcoming that it is affected largely by change and error in the conversion efficiency and also by alteration in the concentration of ozone monoxide in the atmospheric air.

There is also a technique in which molecules of nitrogen dioxide are excited by a laser light and the intensity of a fluorescent light emitted when the excited nitrogen dioxide molecules return to their ground state is measured to determine the concentration of nitrogen dioxide. Its principles are explained below.

A nitrogen dioxide molecule $NO_2$ to transition from its ground state $^2A_1$ to its excited state $^2B_2$ absorbs a photon of frequency $v_1$ having the energy required for the transition to form a nitrogen dioxide molecule $NO_2^*$ in the excited state, following the reaction:

$$NO_2^* + hv_1 \rightarrow NO_2^* \qquad (1)$$

The nitrogen dioxide molecule $NO_2^*$ in the excited state upon emitting a photon of frequency $v_2$ deviated towards red relative to frequency $v_1$ is returned to a nitrogen dioxide molecule $NO_2$ in the ground state as follows:

$$NO_2^* \rightarrow NO_2 + hv_2 \qquad (2)$$

Since the reaction (1) is proportional to the concentration of nitrogen dioxide molecules $NO_2$, the number of photons of frequency $v_2$ is proportional to the concentration of nitrogen dioxide molecules $NO_2$. It is thus possible to determine the concentration of nitrogen dioxide molecules $NO_2$ by exciting the nitrogen dioxide molecules $NO_2$ with a laser light and measuring the number of photons emitted by the nitrogen dioxide molecules $NO_2$ in the excited state.

However, not only do those incident on a photon counting instrument include photons emitted in the form of a fluorescent light from nitrogen dioxide molecules, but also they include photons incident due to the scattering (Rayleigh scattering and Mie scattering) of the excited laser light by a particulate matter (aerosols) in the atmospheric air. Since the concentration to be measured here is in the pptv order of magnitude, an extremely feeble signal or a signal that is low in signal/noise ratio makes it impossible to accurately measure the concentration of nitrogen dioxide unless the scattered light intensity as a background noise is subtracted from the measured light intensity.

In addition to that due to the light scattering by the particulate matter, such background noises include those due to dark current from the photon detector and irregular reflections of light by instrument walls, which must also be subtracted in order to allow the concentration of nitrogen dioxide to be accurately determined.

A nitrogen dioxide concentration measurement apparatus designed to overcome these difficulties exists utilizing a dual wavelength laser induced fluorescence technique using a variable wavelength pulsed light laser. In this technique, two laser lights having their wavelengths corresponding to a peak and a valley of the absorption spectrum of nitrogen dioxide, respectively, are alternately applied for measurement. The first laser light of the wavelength corresponding to the peak of the absorption spectrum excites nitrogen dioxide molecules, and then there results a measure value that is the sum of the intensity of fluorescence emitted by nitrogen dioxide molecules, the intensity of scattered lights by the particulate matter and the other background noises. On the other hand, the second laser light of the wavelength corresponding to the valley of the absorption spectrum of nitrogen dioxide does not excite the nitrogen dioxide molecules, and then there results a measured value that is the sum of the scattered lights by the particulate matter and the other background noises.

It follows, therefore, that subtracting the measured value by the laser light of the wavelength corresponding to the valley from the measured value by the laser light of the wavelength corresponding the peak allows only the light intensity of the fluorescence from the nitrogen dioxide molecules to be known and thus the concentration of nitrogen dioxide to be determined.

According to this technique, however while it is made possible to measure a concentration of nitrogen dioxide at a level of several of pptv, such a variable wavelength laser becomes essential and indispensable that it can produce two laser lights having wavelengths adjacent to each other and corresponding to the peak and valley of the absorption spectrum of nitrogen dioxide, respectively, and further whose intensity ratio can be strictly controlled. Such a variable wavelength laser is not only expensive but also unstable in operation unavoidably by reason of its operating principles. In order to be made operable stably, it requires elaborate and large-scaled accessories, which are not suitable for an instrument that requires that measurements such as of global atmospheric environments be made simply and easily and regardless of places and seasons.

Under these circumstances, there has presently been no means or apparatus that allows the concentration of nitrogen dioxide as low as at a pptv level to be determined simply and easily and at the same time with high precision.

DISCLOSURE OF THE INVENTION

With the aforementioned prior-art problem taken into account, the present invention has for its objects to provide a method of determining a concentration of nitrogen dioxide at a pptv level simply and easily and further with high precision and an apparatus for carrying out the method.

In order to achieve the object mentioned above there is provided in accordance with the present invention an atmospheric nitrogen dioxide concentration determining method by a single wavelength laser induced fluorescence technique, characterized in that the method comprises the steps of: sampling a test atmosphere from an ambient atmosphere containing nitrogen dioxide of which a concentration is as low as in the pptv (volume concentration unit in $10^{-12}$) order of magnitude and providing a reference atmosphere from the test atmosphere by removing nitrogen dioxide therefrom; irradiating each of the test atmosphere and the reference atmosphere with a laser light; measuring intensity of a light emitted from the test atmosphere and intensity of a light emitted from the reference atmosphere with a single-wavelength laser light having an energy of exciting a nitrogen dioxide molecule from its ground state $^2A_1$ to its excited state $^2B_2$; and subtracting the intensity of the light emitted from the reference atmosphere from the intensity of the light emitted from the test atmosphere to determine the concentration of nitrogen dioxide in the test atmosphere which is as low as in the pptv order of magnitude. The said single-wavelength laser light having an energy of exciting a nitrogen dioxide molecule from its ground state $^2A_1$ to its excited state $^2B_2$ is characterized in that it is a visible light having a wavelength of 532 nm.

According to this method, a measured value for a test atmosphere irradiated with a laser light contains the intensity of a fluorescent light from nitrogen dioxide, the intensity of scattered lights by a particulate matter in the atmospheric air, the light intensity of irregular reflections by interior components of the apparatus and the background signals such as dark current from the photon detector. On the other hand, a measured value for a reference atmosphere irradiated with the laser light contains the intensity of the scattered lights by the particulate matter in the atmospheric air, the light intensity of the irregular reflections by the interior components of the apparatus and the background signals such as dark current from the photon detector as for the test atmosphere, but unlike the test atmosphere does not contain the intensity of the fluorescent light from nitrogen dioxide. Thus, subtracting the measure value for the reference atmosphere irradiated with the laser light from the measured value for the test atmosphere irradiated with the laser light allows determining the intensity of the fluorescent light from nitrogen dioxide and hence the concentration of nitrogen dioxide that is as low as in the pptv order of magnitude accurately.

Further, since a single wavelength laser light source is satisfactory and sufficient and such a multiple-wavelength laser. e. g., two-wavelength dye laser, that it can produce laser lights having wavelengths adjacent to each other is not required, and since the laser power can thus be augmented without necessitating elaborate and large-scale accessories for stable operation it is possible to make a measurement simply and easily.

In the present invention, the method is specifically characterized in that the reference atmosphere having nitrogen dioxide removed is provided by passing the test atmosphere through a diffusion scrubber in the form of a tube having a tube wall coated with powdery titanium oxide. According to this specific feature, a difference in diffusion coefficient between a particulate matter and gaseous components in the atmosphere is utilized on the basis of which only gaseous components are allowed to reach the tube wall where of these gaseous components only nitrogen dioxide is adsorbed by powdery titanium oxide and removed so as to form the reference atmosphere.

Also, the method is specifically characterized in that the said intensity of the light emitted from the test atmosphere and the said intensity of the light emitted from the reference atmosphere are measured in a vacuum of a degree of vacuum at which a radiative relaxation phenomenon that nitrogen dioxide molecules excited by the laser light are relaxed upon radiating a fluorescent light is maximized in occurrence. According to this specific feature, it is possible to produce the fluorescence efficiently and to determine the concentration of nitrogen dioxide accurately.

The present invention also provides an atmospheric nitrogen dioxide concentration determining apparatus implementing a single wavelength laser induced fluorescence technique, characterized in that it comprises: a single-wavelength, pulsed laser light source means for generating a pulsed laser light of a wavelength having an energy of exciting a nitrogen dioxide molecule from its ground state $^2A_1$ to its excited state $^2B_2$; a photoexciting means for passing the pulsed laser light from the pulsed laser light source means through atmospheric air to excite the atmospheric air; a light lead-in means for guiding the pulsed laser light into the said photoexciting means; an atmosphere conducting means for guiding each of a test atmosphere and a reference atmosphere having nitrogen dioxide removed from the test atmosphere by passing the test atmosphere through a diffusion scrubber in the form of a tube having a tube wall coated with powdery titanium dioxide, selectively to the said photoexciting means a light detecting means for measuring intensity of a light emission produced in the said photoexciting means; and a control means for controlling the time sequence of operations of the said pulsed laser light source means and the said light detecting means and also processing detection signals issued from the said light detection means to display a processing result. With the apparatus so constructed, it is possible to determine a concentration of nitrogen dioxide which as low as at a pptv level, simply and easily and at the same time with high precision.

The said pulsed laser light source means preferably includes a Nd:YAG laser unit and a second harmonic generator and is adapted to emit a pulsed laser light having a wavelength of 532 nm. According to this specific feature, a pulsed laser light of 532 nm in wavelength that can excite nitrogen dioxide molecules can be generated stably and with an increased intensity.

The said photoexciting means preferably includes a photoexciting cell, and a light incident and a light exit tube connected to side walls of the said photoexciting cell so that they extend coaxially for passing the pulsed laser light through the said photoexciting means to excite the atmosphere therein.

Each of the said light incident and exit tubes preferably is sealed hermetically at its outer end with an inclined light transmissive window and is provided with a plurality of baffle plates to prevent scattered lights of the passing laser light from entering the said photoexciting cell. According to this specific feature, it is possible to excite $NO_2$ in the atmosphere efficiently while minimizing the background signals due to irregular light reflections caused by interior components of the apparatus.

The apparatus is specifically characterized in that the said atmosphere conducting means includes an atmosphere selective supply for supplying the said photoexciting cell with one of the said test atmosphere and the said reference atmosphere selectively, and an air exhauster for venting the atmosphere supplied to the said photoexciting cell, whereby the said test atmosphere and the said reference atmosphere when selected are formed to flow as a laminar flow.

The said atmosphere selective supply and the said air exhauster are specifically characterized in that they are connected to the side walls of the said photoexciting cell so that the said laminar flow of the atmosphere flows orthogonally to the optical path of the said pulsed laser light.

The said atmosphere selective supply is specifically characterized in that it comprises a blank tube for supply of the said test atmosphere, a diffusion scrubber for supply of the said reference atmosphere, an atmosphere inlet port to which the said blank tube and the said diffusion scrubber are connected in parallel through their respective first open ends for introducing the atmospheric air into the said blank tube and the said diffusion scrubber, respectively, and a three-way solenoid valve disposed between respective second open ends of the said blank tube and the said diffusion scrubber and connected to the said photoexciting cell for supplying the latter with one of the said test and reference atmospheres selectively. The said diffusion scrubber is specifically characterized in that it comprises a glass tube having an inner wall coated with powdery titanium oxide.

With the apparatus so constructed specifically, it is possible to switch the test and reference atmospheres from one to the other quickly, to supply the photoexciting cell therewith stably and to form the laminar flow thereof flowing stably.

Also, the said atmosphere selective supply preferably includes an orifice disposed directly adjacent to the said photoexciting cell whereby venting resistance can be increased to create a pressure at which the intensity of fluorescence is maximized. The orifice has its diameter, preferably of 0.3 mm.

According to this specific feature, the non-radiative relaxation phenomena can be minimized that the excited nitrogen dioxide molecules upon colliding with fine particulate matters, nitrogen molecules and oxygen molecules are returned to their ground state without light emission. Hence, the fluorescent intensity for nitrogen dioxide can be maximized, thereby raising the S/N ratio of measurement.

The said light detecting means preferably comprises a light condensing mirror and convex lenses for collecting light emitted from the atmosphere in a region where the said pulsed laser light and the said laminar flow intersect orthogonally, a photon detector for detecting an intensity of the light collected, and an optical filter disposed directly in front of the said photon detector. And, the said light detecting means can be connected to a side wall of the said photoexciting cell so that its optical axis intersects orthogonally with the optical path of the said pulsed laser light and the said laminar flow.

According to this specific feature, it is possible to detect practically all the light emitted from the atmosphere and to diminish the irregular light reflections caused within the optical filter, and hence to raise the S/N ratio of measurement.

Further, the said control means includes a system clock generator for generating system clocks on the basis of which a timing is taken for the said pulsed laser light source to issue the pulses laser light wherein on the basis of the said timing a timing is taken for the said light detecting means to measure a value of each of the said test and reference atmospheres, and the said control means is adapted to accumulate such measured values of the said test atmosphere and such measured values of the said reference atmosphere which measured values for each of the said test and reference atmosphere are derived by a plurality of measurements whereby the concentration of nitrogen dioxide in the said test atmosphere is determined by processing the measured values of the said test atmosphere and the measured values of the said reference atmosphere accumulated and is displayed. According to this specific feature, it is possible to make a plurality of measurements accurately and in a short period of time to accumulate them. This reduces their statistical errors and allows the concentration of nitrogen dioxide in the test atmosphere to be determined with an increased accuracy.

What is more, the said light intensity is preferably detected by the said photon detector utilizing photon counting technique. According to this feature, it is possible to determine an extremely low concentration of nitrogen dioxide.

BRIEF DESCRIPTION OF THE DRAWINGS

The present invention will better be understood from the following detailed description and the drawings attached hereto showing certain illustrative forms of embodiment of the present invention. In this connection, it should be noted that such forms of embodiment illustrated in the accompanying drawings hereof are intended in no way to limit the present invention but to facilitate an explanation and understanding thereof. In the drawings.

BEST MODES FOR CARRYING OUT THE INVENTION

Figure 1:
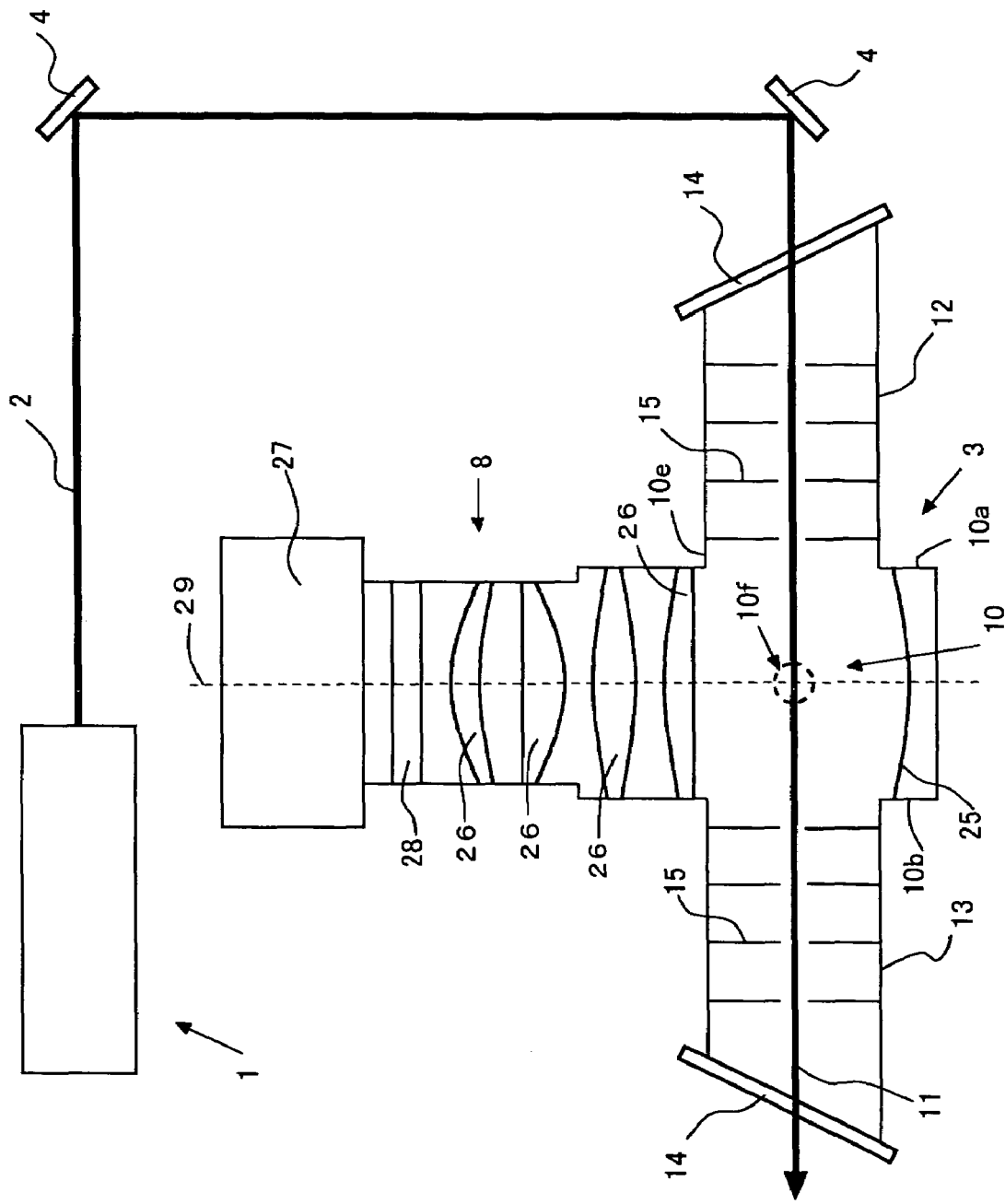
FIG. 1 is a diagram illustrating the makeup of an optical system in an atmospheric nitrogen dioxide concentration determining apparatus in which the determination is made by laser induced fluorescence technique using a single laser wavelength in accordance with the present invention.

Hereinafter, the present invention with respect to an atmospheric nitrogen dioxide concentration determining method and apparatus utilizing a laser induced fluorescence technique using a single laser wavelength will be described in detail with reference to forms of implementation thereof illustrated in the drawing figures.

Figure 2:
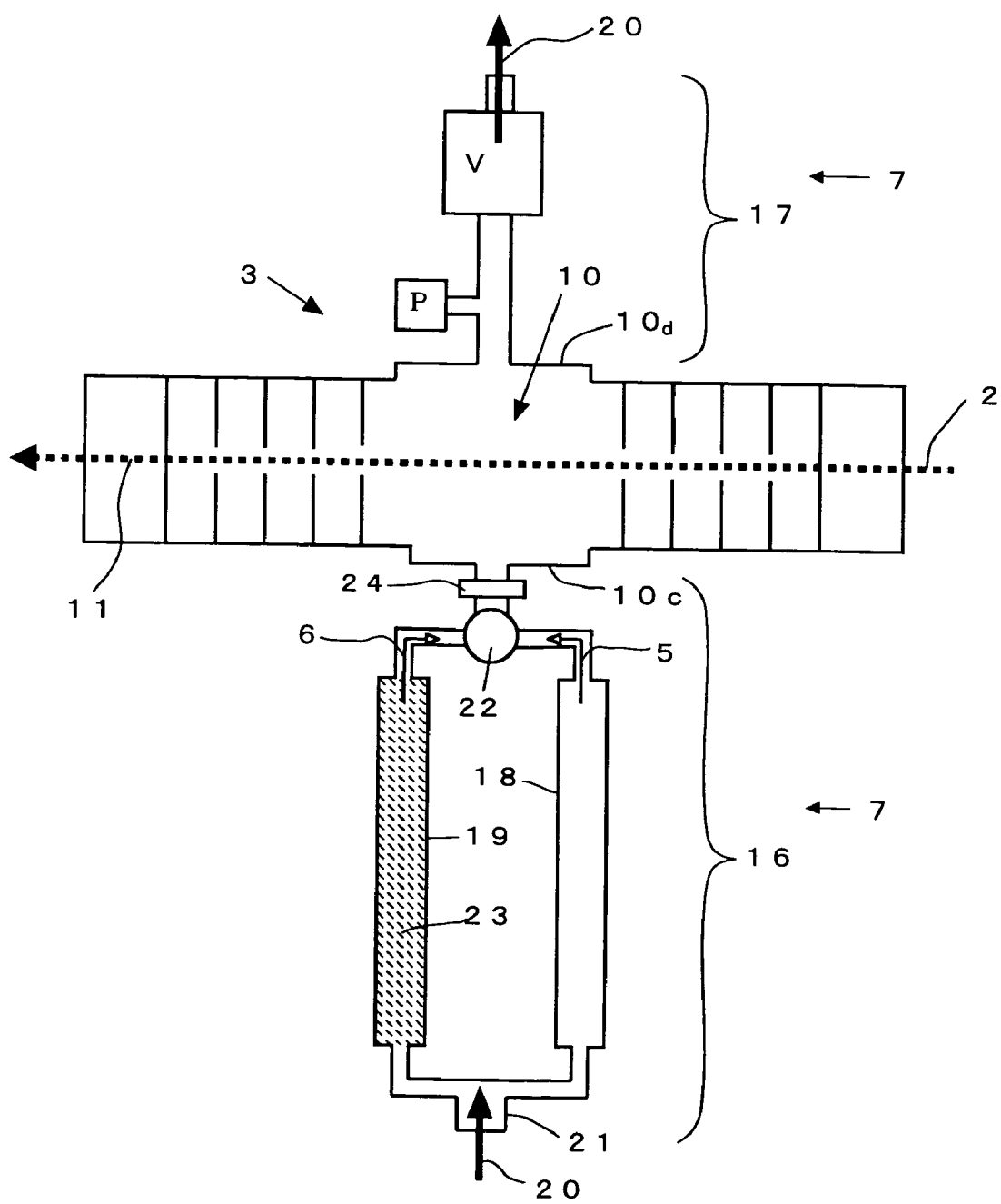
FIG. 2 is a diagram illustrating the makeup of an atmospheric air inlet system in an atmospheric nitrogen dioxide concentration determining apparatus in which the determination is made by laser induced fluorescence technique using a single laser wavelength in accordance with the present invention.
Figure 3:
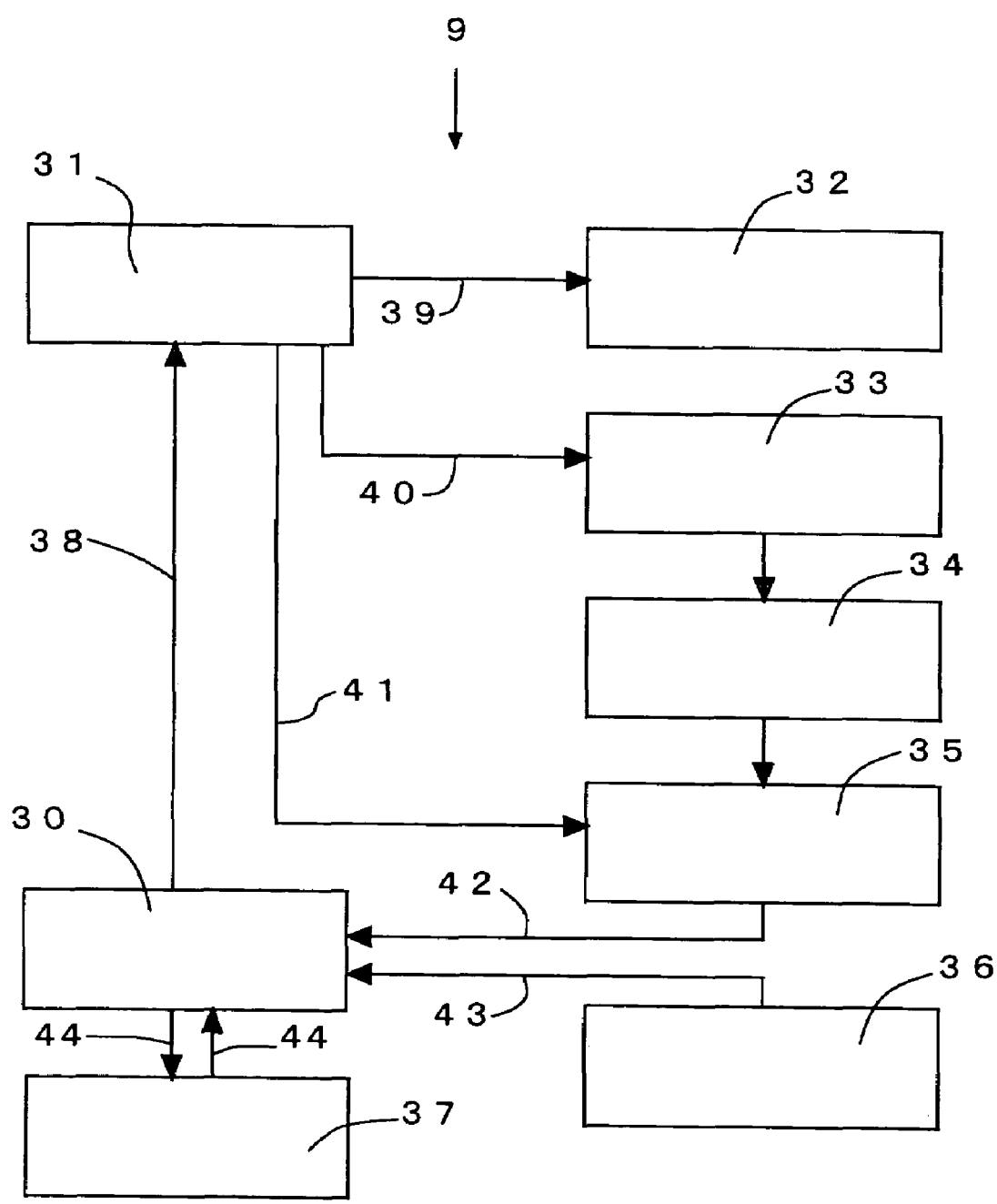
FIG. 3 is a diagram illustrating the makeup of a control system in an atmospheric nitrogen dioxide concentration determining apparatus in which the determination is made by laser induced fluorescence technique using a single laser wavelength in accordance with the present invention.

FIG. 1 is a diagram illustrating the makeup of an optical system in an atmospheric nitrogen dioxide concentration determining apparatus in which the determination is made by laser induced fluorescence technique using a single laser wavelength in accordance with the present invention. FIGS. 2 and 3 show an atmospheric air inlet system and a control system, respectively, in the apparatus. Mention is first made of the makeup of the apparatus with reference to FIGS. 1 to 3:

The apparatus illustrated includes a pulsed laser light source section 1, a photoexciting section 3 for exciting atmospheric air by passing therethrough a pulsed laser light 2 from the pulsed laser light source section 1, a light lead-in section 4 for guiding the pulsed laser light 2 into the photoexciting section 3, an atmosphere conducting section 7 through which each of a test atmosphere 5 and a reference atmosphere 6 having nitrogen dioxide removed from the test atmosphere is selectively conducted and passed, a light detecting section 8 for measuring the intensity of a light emission generated in the photoexciting section 3, and a timing control section 9 whereby the time sequence of operations of the pulsed laser light source section 1 and the light detecting section 8 is controlled and detection signals issued from the latter are processed to display a result of the processing.

The pulsed laser light source section 1 preferably comprises a combination of an Nd:YAG laser unit and a $2^{nd}$ harmonic generator, which is designed to issue a pulsed laser light having a wavelength of 532 nm and a power of 6.5 W, the pulsed laser light being iteratively issued at a repetition rate of 10 kHz.

The photoexciting section 3 includes a photoexciting cell 10, and a light entrance and a light exit tube 12 and 13 connected to mutually opposing side walls 10a and 10b of the photoexciting cell 10, respectively, so that they extend coaxially with each other as shown by the arrow 11. Their function is to pass a pulsed laser light 2 through the photoexciting section 3 and thereby to photoexcite the test atmosphere 5 and the reference atmosphere 6 individually.

Each of the light entrance and exit tubes 12 and 13 is hermetically sealed with a transparent or light transmissive window 14, 14 provided at its outer end and is provided with a plurality of baffle plates 15 in series so that scattered light components of the passing pulsed laser light 2 may not enter the photoexciting cell 10. Indicated by reference character 10f is an area where an atmosphere selective supply 16 to be described below is connected to the photoexciting cell 10.

The atmosphere conducting section 7 comprises the atmosphere selective supply 16 for selectively supplying the test atmosphere 5 and the reference atmosphere 6 into the photoexciting cell 10 and an exhauster 17 for venting the atmosphere supplied to the photoexciting cell 10, whereby each of the test atmosphere 5 and the reference atmosphere 6 flows in a laminar flow past the photoexciting cell 10. The exhauster 17 includes a vacuum pump V and a vacuum meter P and is thereby designed to make the rate at which the atmosphere is vented variable.

The atmosphere selective supply 16 and the exhauster 17 are connected to mutually opposing side walls 10c and 10d of the photoexciting cell 10, respectively, so that the laminar flow of the atmosphere runs orthogonally to the optical path 11 of the pulsed laser light. The atmosphere selective supply 16 as noted above is connected to a central area 10f of the side wall 10c.

The atmosphere selective supply 16 comprises a blank tube 18 for the supply of the test atmosphere 5, a diffusion scrubber 19 for the supply of the reference atmosphere 6, an air inlet port 21 with which the blank tube 18 and the diffusion scrubber 19 communicate in parallel each through its one open end for accepting an ambient atmosphere or atmospheric air 20 therein, and a three-way solenoid valve 22 connected between the respective other open ends of the blank tube 18 and the diffusion scrubber 19 and connecting to the photoexciting cell 10 for supplying the latter selectively with one of the test atmosphere 5 and the reference atmosphere 6 supplied from the blank tube 18 and the diffusion scrubber 19, respectively.

The diffusion scrubber 19 comprises a glass tube having its inner wall coated with powdery titanium oxide 23. With the scrubber 19 so made up, a difference between the diffusion coefficients of a particulate matter and gaseous components in the atmospheric air 20 allows the gaseous components selectively to reach the tube wall of the scrubber 19 and nitrogen dioxide selectively of the gaseous components to be adsorbed by the titanium oxide powder whereby the reference atmosphere 6 composed of the atmospheric air 20 with nitrogen dioxide removed therefrom is formed.

The atmosphere selective supply 16 provided with the exhauster 17 has an orifice 24 in close proximity to the photoexciting cell 10 such that the exhauster 17 and the orifice 24 jointly provide an optimum pressure at which the intensity of a fluorescent light emitted becomes the maximum. The orifice 24 has a diameter preferably of 0.3 mm.

Not only are nitrogen dioxide molecules returned to the ground state upon emitting fluorescence but also they may be returned to the ground state upon colliding with fine particulate matters, nitrogen molecules, oxygen molecules and so on in the atmosphere but without light emission or radiation. If the atmospheric pressure is reduced, the probability of collisions with fine particulate matters, nitrogen molecules, oxygen molecules and so on is lowered and non-radiative relaxation phenomena are lessened in occurrence, but at the same time the concentration of fluorescence emitting nitrogen dioxide is reduced and the radiative relaxation phenomena are lessened in occurrence. On the basis of collision cross section and radiative quantum efficiency, there exists a pressure at which the ratio in occurrence of radiative relaxation phenomena to non-radiative relaxation phenomena can be maximized. See J. Matsumoto et al. Atmospheric Environment 35 (2001) 2803-2814.

According to the apparatus illustrated, a laminar flow of atmosphere that maximizes the intensity of fluorescence is created with the orifice 24 to increase the flow rate of the atmosphere without disturbing the laminar flow. The fluorescence intensity has been found to become the maximum when the atmospheric pressure is adjusted at 0.5 to 1.0 Torr.

The light detecting section 8 comprises a condensing mirror 25 and a series of convex lenses 26 for collecting light rays emitted from the atmosphere in an area where the laminar flow and the optical axis 11 of the pulsed laser light 2 intersect orthogonally, a photon detector 27 for detecting the intensity of the light collected, and an optical filter 28 disposed immediately in front of the photon detector 27. The photon detector 27 preferably comprises a photo multiplier tube (PMT). The optical filter 28 is provided to diminish photons other than those of the fluorescent light being incident on the photon detector 27, and preferably is designed to cut photons of wavelengths of 640 nm or less. The light detecting section 8 is connected to a side wall. 10$e$ of the photoexciting cell 10 so that its optical axis 29 intersects orthogonally with the optical path 11 of the pulsed laser light 2 and with the laminar flow of the atmosphere.

Mention is next made of the control section 9. The control section 9 comprises a processing and control unit 30, a system clock generator 31, a laser emission controller 32 incorporated into the pulsed laser light source section 1, a photon detector controller 33 incorporated into the photon detector 27, a photon counter 34 for counting the number of photons incident on the photon detector 27, a detected signal gate 35 for controlling the delivery of photon count information derived from the photon counter 34 to the processing and control unit 30, a laser fluctuation compensator 36 incorporated into the pulsed laser light source section 1 for compensating for laser fluctuations, and a flow path controller 37 for maintaining the atmospheric laminar flow in a given state. The control section 9 operates the apparatus as follows: The processing and control unit 30 delivers a control signal 38 indicating a start of measurement to the system clock generator 31. Upon receiving the control signal 38, the system clock generator 31 generates system clocks and counts them, issuing control signals when given numbers of system clocks have been counted, respectively, in the order mentioned below.

The system clock generator 31 first issues a control signal 39 and delivers it to the laser emission controller 32 to cause the latter to emit a pulsed laser light 2. Then, the system clock generator 31 issues a control signal 40 at a given subsequent time instant and delivers it to the photon detector controller 33 to enable the photon detector 27 to detect and the photon counter 34 to count photons. Then, the system clock generator 31 issues a control signal 41 at a given subsequent time instant and delivers it to the detected signal gate 35 to cause the latter to deliver count information 42 to the processing and control unit 30.

A cycle of the abovementioned steps is repeated a plurality of times for each of the test atmosphere 5 and the reference atmosphere 6, and a cumulative value representing the numbers of photons emitted from each of the test atmosphere 5 and the reference atmosphere 6 is stored in the processing and control unit 30. On the basis of a difference between an accumulated measuring value for the test atmosphere 5 and an accumulated measurement value for the reference atmosphere 6, the processing and control unit 30 displays the concentration of nitrogen dioxide. Also, the processing and control unit 30 successively receives action information 43 for the pulsed laser light source section 1 from the laser fluctuation compensator 36 to furnish the laser emission controller 32 with a control signal 38 such as to operate the pulsed laser light source section 1 stably. Further, the processing and control unit 30 exchanges information and control signals 44 with the flow path controller 37 to maintain the atmospheric laminar flow substantially constant.

Thus, according to the method and apparatus of the present invention, a concentration of nitrogen dioxide as low as in the pptv order of magnitude can be determined simply and easily and at the same time with high accuracy by virtue of the use of a semiconductor excited laser that is easy to handle and highly stable and of a diffusion scrubber that can be used simply and easily to form a reference atmosphere. For example, a limit of detection of 4 pptv has been found possible for a cumulative time period of 60 seconds.

A specific example of the present invention follows.

A real atmosphere measurement was conducted at Rishiri Island, Hokkaido wherein a concentration of nitrogen dioxide was measured using an apparatus according to the present invention to give rise to a measured value represented as [$NO_2$], At the same time, the concentrations of NO, $O_3$, $HO_2$ and $RO_2$ (peroxyl radicals) were measured by using other techniques to give rise to measured values represented as [NO], [$O_3$], [$HO_2$] and [$RO_2$], respectively. Using these measured values [$NO_2$], [NO], [$O_3$], [$HO_2$] and [$RO_2$] and $J_{NO2}$ (photodissociation coefficient of nitrogen dioxide), the measured values of [$NO_2$]/[NO] are compared with its calculated values which can be given by the equation below.

$$[NO_2]/[NO]=(k_1[O_3]+k_2[HO_2]+k_3[RO_2])/J_{NO2}$$

where $k_1$, $k_2$, and $k_3$ are the coefficients of extinction ratio of $O_3$, $HO_2$ and $RO_2$, respectively.

Figure 4:
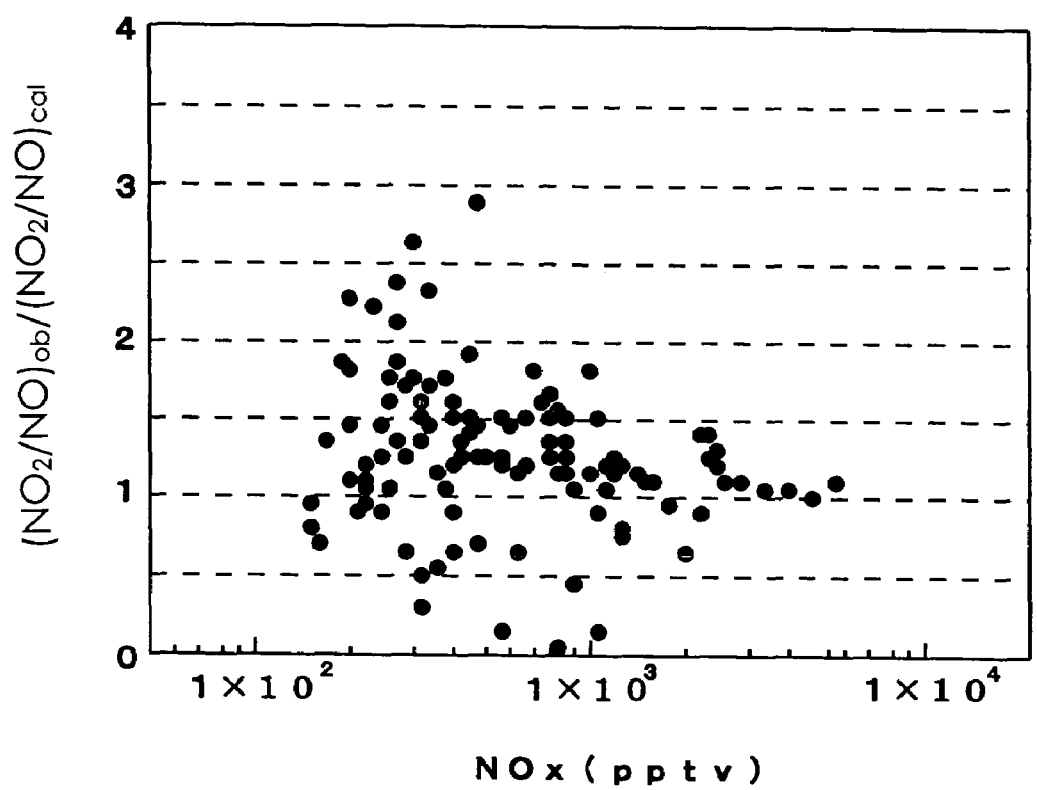
FIG. 4 is a graph showing results of comparison of the measured values by the apparatus according to the present invention with the calculated values for [$NO_2$]/[$NO$]

FIG. 4 is a graph showing results of comparison of the measured values with the calculated values for [$NO_2$]/[NO] wherein the total amount of nitrogen oxide NOx is plotted along the abscissa axis and the ratio of the measured value to the calculated value is plotted along the ordinate axis. In the graph, the tendency is seen that a measured value is greater than a calculated value. This tendency, which is due to the fact that halogen oxide in the ocean atmosphere converts NO to $NO_2$, could not be observed by the conventional techniques. It is thus shown that the present invention has made it possible to determine with high precision a concentration of nitrogen dioxide which it has been impossible for the prior art to determine.

A specific example is next given of the capability of a diffusion scrubber in the present invention. In the method of the present invention, of the components which constitute a measured value it is necessary to know a background component other than that by the fluorescence of nitrogen dioxide. Since the background component is largely affected by the particulate matter in the atmosphere, it is necessary to leave the particulate matter as it is and to form a reference atmosphere containing the same with only nitrogen dioxide removed.

The diffusion scrubber used in experiments is a tube having an inner diameter of 8 mm and a length of 30 cm and having its inner wall coated with powdery titanium oxide. A particle counter was used to measure the concentrations of the particulate matter in the atmosphere before and after it was passed through the diffusion scrubber, and these concentrations were compared with each other.

Figure 5:
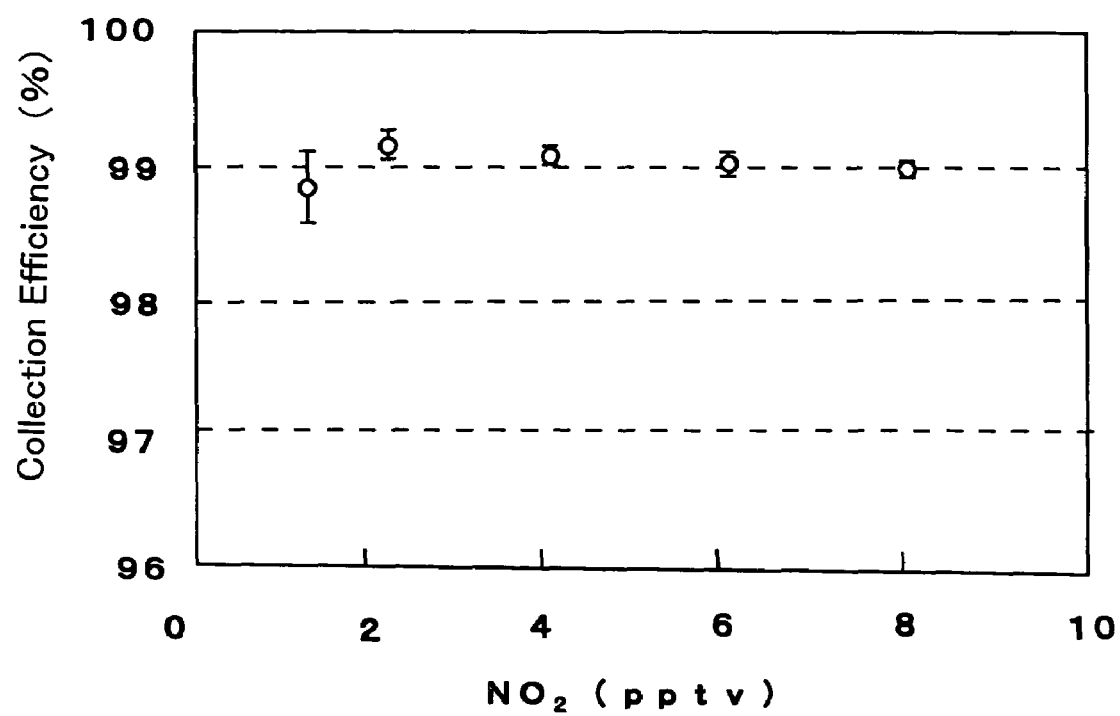
FIG. 5 is a graph illustrating particulate matter removing characteristics of a diffusion scrubber according to the present invention.

FIG. 5 is a graph showing the collection efficiency of $NO_2$ of this diffusion scrubber in various concentrations of $NO_2$ in the atmosphere, wherein ordinate axis represents the collection efficiency and abscissa axis represents concentration of $NO_2$ in the atmosphere. Also, at each of the concentrations, the particulate matter removal ratio were measured by a particle counter, wherein the ratio is the ratio of the lost concentration of the particulate matter in the atmosphere after it was passed through the diffusion scrubber and the concentration of the particulate matter in the atmosphere before it was passed through the diffusion scrubber.

As is apparent from the graph, it is seen that the collection efficiency of $NO_2$ of this diffusion scrubber in various concentrations of $NO_2$ in the atmosphere is about 99%. And it is confirmed that the particulate matter removal ratio is within 5%. This indicates that the method of the present invention is a method enough to identify the background.

INDUSTRIAL APPLICABILITY

It will be appreciated from the foregoing description that according to the present invention, a concentration of nitrogen dioxide contained as little as at a pptv level in the atmosphere can be determined simply and easily and at the same time with high precision. By virtue of a convenient and high-precision atmospheric nitrogen dioxide concentration determining apparatus according to the present invention, it becomes possible to measure nitrogen dioxide concentration conveniently in various parts of the world regardless of areas, altitudes or seasons and to make clear the behaviors of nitrogen dioxide on the global scale.

What is claimed is:

1. An atmospheric nitrogen dioxide concentration determining method by a single-wavelength laser induced fluorescence technique, characterized in that it comprises the steps of:

sampling a test atmosphere from an ambient atmosphere containing nitrogen dioxide of which a concentration is as low as in the pptv order of magnitude and providing a reference atmosphere from the test atmosphere by removing nitrogen dioxide therefrom;

irradiating each of the test atmosphere and the reference atmosphere with a single-wavelength laser light having an energy of exciting a nitrogen dioxide molecule from its ground state $^2A_1$ to its excited state $^2B_2$;

measuring intensity of a light emitted from the test atmosphere and intensity of a light emitted from the reference atmosphere; and subtracting the intensity of the light emitted from the reference atmosphere from the intensity of the light emitted from the test atmosphere to determine the concentration of nitrogen dioxide in the test atmosphere which is as low as in the pptv order of magnitude.

2. An atmospheric nitrogen dioxide concentration determining method by single-wavelength laser induced fluorescence technique as set forth in claim 1, characterized in that said reference atmosphere having nitrogen dioxide removed is provided by passing said test atmosphere through a diffusion scrubber in the form of a tube having a tube wall coated with powdery titanium oxide.

3. An atmospheric nitrogen dioxide concentration determining method by a single-wavelength laser induced fluorescence technique as set forth in claim 1, characterized in that said intensity of the fluorescence light emitted from the test atmosphere and said intensity of the fluorescence light emitted from the reference atmosphere are each measured in a vacuum of a degree of vacuum at which a radiative relaxation phenomenon that nitrogen dioxide molecules excited by the laser light are relaxed upon radiating a fluorescent light is maximized in occurrence.

4. An atmospheric nitrogen dioxide concentration determining apparatus implementing a single-wavelength laser induced fluorescence technique, characterized in that it comprises:

a pulsed single-wavelength laser light source means for generating a pulsed laser light of a wavelength having an energy of exciting a nitrogen dioxide molecule from its ground state $^2A_1$ to its excited state $^2B_2$;

a photoexciting means for passing the pulsed laser light from the pulsed single-wavelength laser light source means through atmospheric air to excite the atmospheric air;

a light lead-in means for guiding the pulsed laser light into said photoexciting means;

an atmosphere conducting means for guiding each of a test atmosphere and a reference atmosphere having nitrogen dioxide removed from the test atmosphere by passing the test atmosphere through a diffusion scrubber in the form of a tube having a tube wall coated with powdery titanium dioxide, selectively to said photoexciting means;

a light detecting means for measuring intensity of a light emission produced in said photoexciting means;

and a control means for controlling the time sequence of operations of said pulsed laser light source means and said light detecting means and also processing detection signals issued from said light detection means to display a processing result, whereby a concentration of nitrogen dioxide in said test atmosphere is determined which is as low as in the pptv order of magnitude.

5. An atmospheric nitrogen dioxide concentration determining apparatus implementing a single-wavelength laser induced fluorescence technique as set forth in claim 4, characterized in that said pulsed laser light source means includes an Nd: YAG laser unit and a second harmonic generator and is adapted to emit a pulsed laser light having a wavelength of 532 nm.

6. An atmospheric nitrogen dioxide concentration determining apparatus implementing a single-wavelength laser induced fluorescence technique as set forth in claim 4, characterized in that said photoexciting means includes a photoexciting cell, and a light incident and a light exit tube connected to side walls of said photoexciting cell so that they extend coaxially for passing the pulsed laser light through said photoexciting means to excite the atmosphere therein.

7. An atmospheric nitrogen dioxide concentration determining apparatus implementing a single-wavelength laser induced fluorescence technique as set forth in claim 6, characterized in that each of said light incident and exit tubes is sealed hermetically at its outer end with an inclined light transmissive window and is provided with a plurality of baffle plates to prevent scattered lights of the passing laser light from entering said photoexciting cell.

8. An atmospheric nitrogen dioxide concentration determining apparatus implementing a single-wavelength laser induced fluorescence technique as set forth in claim 4, characterized in that said atmosphere conducting means includes an atmosphere selective supply for supplying said photoexciting cell with one of said test atmosphere and said reference atmosphere selectively, and an air exhauster for venting the atmosphere supplied to said photoexciting cell, whereby said test atmosphere and said reference atmosphere when selected are formed to flow as a laminar flow.

9. An atmospheric nitrogen dioxide concentration determining apparatus implementing a single-wavelength laser induced fluorescence technique as set forth in claim 8, characterized in that said atmosphere selective supply and said air exhauster are connected to the side walls of said photoexciting cell so that said laminar flow of the atmosphere flows orthogonally to the optical path of said pulsed laser light.

10. An atmospheric nitrogen dioxide concentration determining apparatus implementing a single-wavelength laser induced fluorescence technique as set forth in claim 8, characterized in that said atmosphere selective supply comprises a blank tube for supply of said test atmosphere, a diffusion scrubber for supply of said reference atmosphere, an atmosphere inlet port to which said blank tube and said diffusion scrubber are connected in parallel through their respective first open ends for introducing the atmospheric air into said blank tube and said diffusion scrubber, respectively, and a three-way solenoid valve disposed between respective second open ends of said blank tube and said diffusion scrubber and connected to said photoexciting cell for supplying the latter with one of said test and reference atmospheres selectively.

11. An atmospheric nitrogen dioxide concentration determining apparatus implementing a single-wavelength laser induced fluorescence technique as set forth in claim 10, characterized in that said diffusion scrubber comprises a glass tube having an inner wall coated with powdery titanium oxide.

12. An atmospheric nitrogen dioxide concentration determining apparatus implementing a single-wavelength laser induced fluorescence technique as set forth in claim 8, characterized in that said atmosphere selective supply includes an orifice disposed directly adjacent to said photoexciting cell whereby venting resistance can be increased to create a pressure at which the intensity of fluorescence is maximized.

13. An atmospheric nitrogen dioxide concentration determining apparatus implementing a single-wavelength laser induced fluorescence technique as set forth in claim 12, characterized in that said orifice has a orifice diameter of 0.3 mm.

14. An atmospheric nitrogen dioxide concentration determining apparatus implementing a single-wavelength laser induced fluorescence technique as set forth in claim 4, characterized in that said light detecting means comprises a light condensing mirror and convex lenses for collecting light emitted from the atmosphere in a region where said pulsed laser light and said laminar flow intersect orthogonally, a photon detector for detecting an intensity of the fluorescence light collected, and an optical filter disposed directly in front of said photon detector.

15. An atmospheric nitrogen dioxide concentration determining apparatus implementing a single-wavelength laser induced fluorescence technique as set forth in claim 14, characterized in that said light detecting means is connected to a side wall of said photoexciting cell so that its optical axis intersects orthogonally with the optical path of said pulsed laser light and said laminar flow.

16. An atmospheric nitrogen dioxide concentration determining apparatus implementing a single-wavelength laser induced fluorescence technique as set forth in claim 4, characterized in that said control means includes a system clock generator for generating system clocks on the basis of which a timing is taken for said pulsed laser light source to issue the pulses laser light wherein on the basis of said timing a timing is taken for said light detecting means to measure a value of each of said test and reference atmospheres, whereby the concentration of nitrogen dioxide in said test atmosphere is determined by processing the measured value of said test atmosphere and the measured value of said reference atmosphere and displayed.

17. An atmospheric nitrogen dioxide concentration determining apparatus implementing a single-wavelength laser induced fluorescence technique as set forth in claim 16, characterized in that said control means is adapted to accumulate such measured values of said test atmosphere and measured values of said reference atmosphere which measured values for each of the said test and reference atmospheres are derived by a plurality of measurements whereby the concentration of nitrogen dioxide in said test atmosphere is determined by processing the measured values of said test atmosphere and the measured values of said reference atmosphere accumulated and is displayed.

18. An atmospheric nitrogen dioxide concentration determining apparatus implementing a single-wavelength laser induced fluorescence technique as set forth in claim 4, characterized in that said light intensity is detected by said photon detector by way of counting photons.

19. An atmospheric nitrogen dioxide concentration determining method as set forth in claim 1, characterized in that said single-wavelength laser light having an energy of exciting a nitrogen dioxide molecule from its ground state $^2A_1$ to its excited state $^2B_2$ is a visible light having a wavelength of 532 nm.

* * * * *